United States Patent [19]

Greene

[11] Patent Number: 4,511,378
[45] Date of Patent: Apr. 16, 1985

[54] LIQUID-GAS CONTACTING APPARATUS AND PUMP THEREFOR

[76] Inventor: George J. Greene, 616 N. Eldridge, Houston, Tex. 77079

[21] Appl. No.: 482,810

[22] Filed: Apr. 7, 1983

Related U.S. Application Data

[63] Continuation of Ser. No. 279,230, Jun. 30, 1981, abandoned.

[51] Int. Cl.³ .............................................. B01D 19/00
[52] U.S. Cl. ........................................ 55/208; 55/228; 417/362; 417/405
[58] Field of Search .......................... 55/208, 227–229; 417/362, 405; 261/36 R

[56] References Cited

U.S. PATENT DOCUMENTS

| | | | |
|---|---|---|---|
| 2,428,643 | 10/1947 | Young | 55/228 X |
| 2,779,291 | 1/1957 | Albright | 417/405 X |
| 2,990,910 | 7/1961 | Kimmell | 55/208 X |
| 3,067,590 | 12/1962 | Wood, Jr. | 417/405 X |
| 3,105,748 | 10/1963 | Stahl | 55/208 X |

FOREIGN PATENT DOCUMENTS 104587 8/1980 Japan ................................... 417/405

Primary Examiner—Kathleen J. Prunner
Attorney, Agent, or Firm—Vinson & Elkins

[57] ABSTRACT

A glycol dehydrator having a contacting vessel, a glycol regenerator and an improved glycol pump which is powered by glycol and gas flowing from the contacting vessel to pump glycol into the contacting vessel. The improved pump includes a positive displacement gear motor, a positive displacement gear pump, and a drive connecting the motor to the pump with the gear motor having a greater volumetric capacity than the gear pump. The gas from the gear motor is separated from the glycol and delivered to the regenerator burner.

4 Claims, 3 Drawing Figures

LIQUID-GAS CONTACTING APPARATUS AND PUMP THEREFOR

CROSS REFERENCE TO RELATING APPLICATION

This application is a continuation of my prior co-pending application, Ser. No. 279,230, filed June 30, 1981, abandoned.

BACKGROUND

Natural gas produced from wells contains water vapor and may contain other compounds such as hydrogen sulphide and sulphur dioxide which are generally preferred to be removed prior to the entry of the gas into a transmission line. Removal of such dilutants and contaminants is desirable to prevent dehydrate blockage, condensed water accumulation and assure proper operation of gas transmission lines by preventing corrosion thereof and to provide the gas which meets the heating value and other specifications usually set by the operator of the transmission line. A general method of removing the water vapor or other material has been to provide intimate contact of the gas with a liquid which will absorb the water or other undesirable material from the stream. Glycol dehydrators are designed to provide intimate contact of the gas stream and triethylene glycol which absorb the water vapor therefrom. Amine desulfurizers have long been used to provide intimate contact between the gas and a monoethanolamine to remove the sulfur compounds from the stream. To preserve the pressure of the natural gas stream produced such intimate liquid gas contact is normally provided in a vessel maintained at substantially the flowing pressure of the natural gas stream and the liquid is pumped into such vessel.

In glycol dehydrators attempts have been made to utilize the wet or rich glycol, i.e. containing water or water vapor, leaving the contacting vessel to provide at least a portion of the driving force to pump the lean or dry regenerated glycol into such vessel as shown in U.S. Pat. Nos. 2,990,910 and 4,026,681. The pump shown in the first mentioned patent has been in use for many years. Such pump is difficult to keep in operation, since it is very complex structure of pistons, check valves, interior slide valves and complex internal porting.

The use of a gear motor driving a gear pump through a direct drive coupling has been suggested (U.S. Pat. No. 3,067,590) for use in a refrigeration system to utilize the liquid flowing in the high pressure side of the system to drive the pumping of low pressure liquid. This is accomplished by interposing a gear motor in the high pressure line leading from the compressor to the accumulator and the gear pump interposed in the low pressure line leading from the accumulator to the evaporators. If such system operates as described, both devices are exposed only to liquid and no gas passes through either device. It appears clear if there is an operable system that the compressor supplies all of the motive power for the movement of the liquids through the system piping. Further, this patent suggests that the pump have a substantially greater cubic displacement than the motor. This clearly negates the passage of gases or vapors through the motor.

Other devices have been suggested to take advantage of fluid energy to move fluids such as U.S. Pat. No. 3,886,763 which provides a single sliding vane compressor-expander for a refrigeration system. A similar unit is shown in the U.S. Pat. No. 3,045,899 which discloses a single sliding vane motor-compressor for use in an absorption system for drying gas. This system suggests that the driving force of a first pressure stream be used to compress a second fluid pressure stream in driving it through a separate circuit.

SUMMARY

The present invention relates to an improved gas-liquid contacting apparatus and to an improved liquid pump. The apparatus includes a vessel to provide intimate contact between the gas and liquid flowing therethrough, a liquid regenerator to remove the materials absorbed in the liquid from the gas and a liquid gear-type pump for pumping regenerated liquid to the contacting vessel which pump is directly driven by a gear motor which is powered by liquid and gas flowing from the contacting vessel. The flow of regenerated liquid is controlled by a single restriction downstream of the discharge from the pump.

An object of the present invention is to provide an improved gas-liquid contacting apparatus which has an improved efficiency in pumping liquid.

Another object is to provide an improved gas-liquid contacting apparatus which efficiently utilizes gas powering the pump for fuel in the regenerator.

A further object is to provide an improved gas-liquid contacting apparatus which is simple and easy to control accurately.

Still another object is to provide an improved liquid pump which is easy to control and relatively maintenance free.

DESCRIPTION OF THE DRAWINGS

These and other objects and advantages of the present invention are hereinafter set forth and explained with reference to the drawings wherein.

DESCRIPTION OF THE PREFERRED EMBODIMENTS

Figure 1:
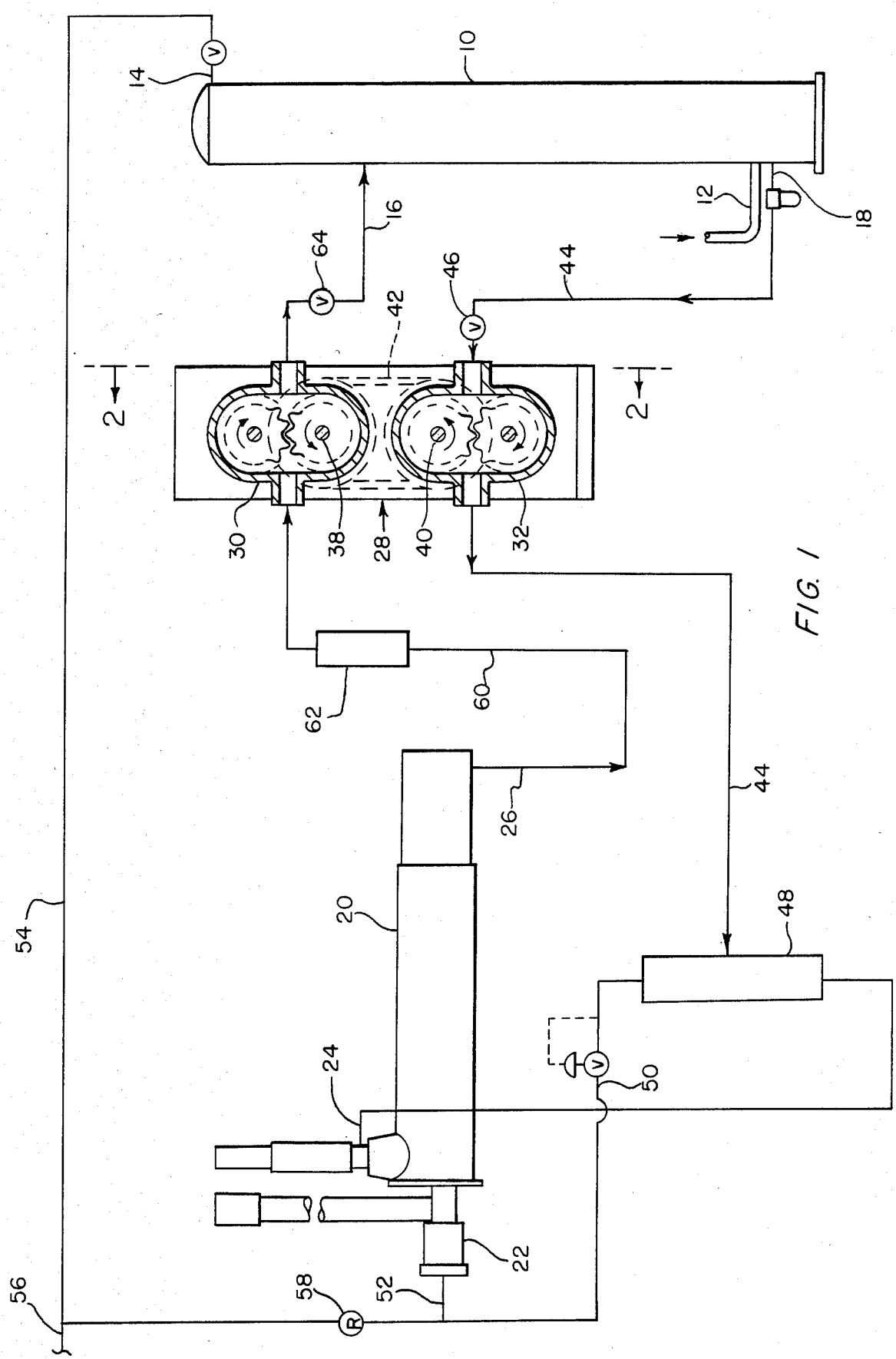
FIG. 1 is a schematic illustration and flow diagram of the improved gas-liquid contacting apparatus of the present invention.

The system illustrated in FIG. 1 is a glycol dehydrator which is used to remove water vapor from a natural gas stream. It should be noted however, that the present invention has application to other gas-liquid contacting processes in which the contact is conducted in a vessel at pressures substantially above atmospheric pressure, such as in a natural gas desulfurization process.

The improved apparatus of the present invention as shown in FIG. 1 includes contacting vessel 10 having gas inlet 12 into the lower portion of vessel 10 and gas outlet 14 from the upper portion of the vessel. Regenerated liquid inlet 16 for dry or lean glycol enters the upper portion of vessel 10 and liquid outlet 18 for wet or rich glycol extends from the lower portion of vessel 10 as shown. The regenerator 20 includes burner 22 which provides the heat necessary to drive the absorbed water from the glycol, a wet liquid or glycol inlet 24 and a regenerated dry liquid or lean glycol outlet 26.

Figure 2:
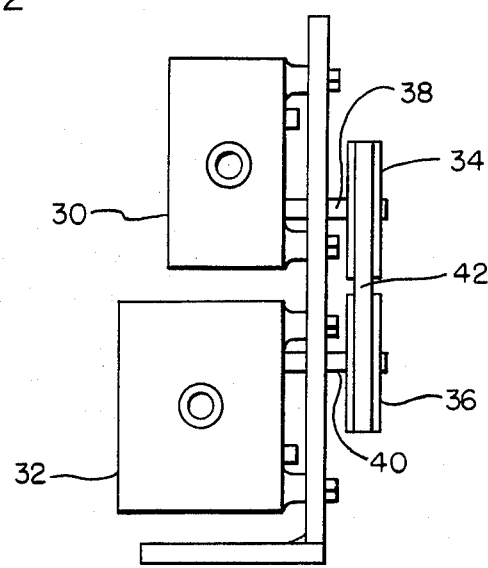
FIG. 2 is a sectional view of the pump taken along lines 2—2 in FIG. 1.

Improved pump or pump structure 28 of the present invention includes a gear-type pump 30, gear-type motor 32 and means providing a driving connection between pump 30 and motor 32. Both pump 30 and motor 32 are positive displacement devices. In FIGS. 1 and 2, drive connecting means includes timing gears 34 and 36 on shafts 38 and 40 of pump 30 and motor 32 and timing belt 42 which engages timing gears 34 and 36 to assure that shafts 38 and 40 rotate simultaneously and at the same speed.

Line 44 connects from wet liquid outlet 18 from vessel 10 to wet liquid inlet 24 in regenerator 20 with gear motor 32 being interposed in line 44. Valve 46, which is preferably used to shut off flow to gear motor 32, is positioned in line 44 ahead of motor 32. Separator 48, having a fluid inlet connected to line 44 from gear motor 32 and a glycol outlet connected to line 44 leading to regenerator 20, is positioned in line 44 between motor 32 and regenerator inlet 24 and functions to provide a gas-liquid separation, delivering liquid through line 44 to regenerator 20 and gas from a gas outlet connected through line 50 to burner fuel supply line 52 for firing burner 22. Additional fuel gas for burner 22 may be supplied from gas outlet 14 of contacting vessel 10 through line 54 or from some other suitable source (not shown) through line 56 both of which are connected to line 52 through pressure regulator 58.

Regenerated lean glycol is supplied from regenerator outlet 26 through line 60 and gear pump 30 to contacting vessel glycol inlet 16. Flow meter 62 is interposed in line 60 between outlet 26 and pump 30 to provide an indication of the rate of flow of lean glycol to contacting vessel 10. Valve 64 is positioned in line 60 between pump 30 and inlet 16 of contacting vessel 10 to control the rate of flow of glycol to vessel 10.

In order to provide sufficient power to pump the lean glycol into contacting vessel 10, a pressure drop of approximately 50 psi should be available to power motor 32. Also, motor 32 is preferred to have a volumetric capacity of 1.2 to 2.0 times the volumetric capacity of pump 30. With adequate pressure differential and such relationship in volume, the flow of glycol and gas through motor 32 is sufficient to drive pump 30.

Also, if two gear units of the same size are to be used the size and number of teeth on timing gears 34 and 36 may be varied to allow a larger volume of liquid and gas to power motor 32 than the volume of liquid pumped by pump 30.

Figure 3:
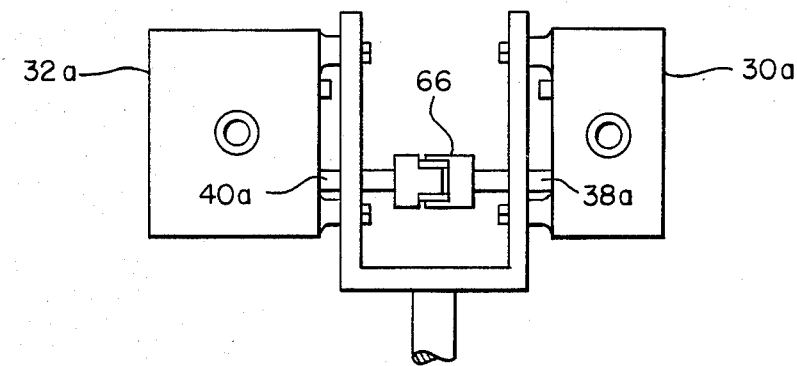
FIG. 3 is a sectional view of a modified form of connection between the gear motor and the gear pump.

The modified form of connection as shown in FIG. 3 between motor 30a and pump 32a provides aligned connection of shafts 38a and 40a which extend from their respective housings. The connecting means is a flexible three-piece coupling 66 including bodies connected onto the ends of the shafts with the spider connecting between the two bodies.

Prior rotary devices have been suggested for such service but have been rejected as unsuitable because their seals do not hold the glycols against high pressure differentials and their shaft seals add greatly to the friction which must be overcome to pump the glycol. The gear-type units used with the present invention provide a venting of the high pressure side of the seal to the suction side of the unit and thus provide a low pressure shaft seal which is accompanied by a minimum of friction.

What is claimed is:

1. A glycol dehydrator, comprising
a contacting vessel having a gas inlet, a gas outlet, a lean glycol inlet, a wet glycol outlet and means within said vessel for providing contact between the gas and the glycol flowing therethrough,
a glycol regenerator,
a first time communicating between the wet glycol outlet and the glycol regenerator,
a second line communicating between the regenerator and the lean glycol inlet,
a gear motor in said first line,
a gear pump in said second line,
means connecting said motor to said pump whereby wet glycol and gas from said contacting vessel provides sufficient power to drive said pump to pump lean glycol into said contacting vessel,
a gas fired burner in contact with said glycol regenerator,
means in said first line between said gear motor and the regenerator for separating gas from wet glycol discharged from said gear motor, and
means for delivering said separated gas to said burner to provide at least a portion of the gas to fire said regenerator burner.

2. A glycol dehydrator comprising
a contacting vessel having a gas inlet, a gas outlet, a lean glycol inlet, a wet glycol outlet and means within said vessel for providing contact between the gas and the glycol flowing therethrough,
a glycol regenerator having a wet glycol inlet, a lean glycol outlet and a burner to heat the glycol within the regenerator whereby water in the wet glycol is vaporized to provide a lean glycol,
a first line connecting from the wet glycol outlet of said contacting vessel to the wet glycol inlet of said glycol regenerator,
a second line connecting from the lean glycol outlet of said regenerator to the lean glycol inlet of said contacting vessel,
a gear motor in said first line to be powered by fluids flowing therethrough,
a liquid-gas separator in said first line between said gear motor and said glycol regenerator and having a fluid inlet connected to the portion of said first line leading from said motor, a glycol outlet connected to the portion of said first line leading to said regenerator and a gas outlet connected to said burner,
a gear pump in said second line to pump lean glycol from said regenerator to said contacting vessel,
a flow control means in said second line downstream of said gear pump to control the rate of flow of lean glycol to said contacting vessel, and
means connecting said motor to said pump whereby wet glycol and gas from said contacting vessel provides sufficient power to drive said pump to pump lean glycol into said contacting vessel,
said motor having a greater volumetric capacity than said pump to allow sufficient gas to pass therethrough with the wet glycol to assure continuous flow of lean glycol at a preselected flow rate to said contacting vessel.

3. In a glycol dehydrator having,
a contacting vessel with a gas inlet and wet glycol outlet, and a gas outlet and lean glycol inlet; and
a glycol regenerator, a first flow line from the glycol regenerator to said lean glycol inlet to provide lean glycol to said vessel, and a second flow line from said wet glycol outlet and vessel in fluid communication with said regenerator to receive wet glycol and gas from the vessel and provide wet glycol to the regenerator for recirculation of the glycol;

the improvement of a glycol pump structure between said vessel and said regenerator comprising:

a positive displacement rotary gear pump in said first flow line between said vessel and said regenerator to provide during operation a continuous uninterrupted flow of lean glycol to said vessel;

a positive displacement rotary gear motor in said second flow line between said vessel and said regenerator to provide during operation a continuous flow of wet glycol and gas from said vessel to said regenerator; and drive means connecting said rotary motor to said rotary pump whereby wet glycol and gas from said contacting vessel to said rotary motor provides sufficient power for said rotary motor to drive said rotary pump for pumping lean glycol into said contacting vessel;

said rotary gear motor having a greater volumetric capacity than said rotary gear pump thereby permitting sufficient gas to pass through the rotary motor with the wet glycol to assure a continuous flow of lean glycol from the rotary pump to said contacting vessel at a preselected flow rate.

4. The glycol dehydrator as set forth in claim 3 wherein said rotary gear motor has a volumetric capacity in the range of 1.2 to 2.0 times the volumetric capacity of said rotary gear pump.

* * * * *